(12) United States Patent
Cropp et al.

(10) Patent No.: US 6,245,787 B1
(45) Date of Patent: *Jun. 12, 2001

(54) COMPOSITION CONTAINING AMLODIPINE OR A PHARMACEUTICALLY ACCEPTABLE SALT THEREOF, AND AN ACE INHIBITOR

(75) Inventors: Anne B. Cropp, Madison; Allen R. Kraska, Old Lyme, both of CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/894,800

(22) PCT Filed: Feb. 26, 1996

(86) PCT No.: PCT/IB96/00145

§ 371 Date: Feb. 26, 1998

§ 102(e) Date: Feb. 26, 1998

(87) PCT Pub. No.: WO96/28185

PCT Pub. Date: Sep. 19, 1996

Related U.S. Application Data

(63) Continuation of application No. 08/405,108, filed on Mar. 16, 1995, now abandoned.

(51) Int. Cl.[7] .......................... A61K 31/44; A61K 31/40; A61K 31/54; A01N 45/00
(52) U.S. Cl. ........................... 514/356; 514/26; 514/423; 514/223.5
(58) Field of Search .................................... 514/356, 278, 514/223.5, 381, 26, 423; 546/321

(56) References Cited

U.S. PATENT DOCUMENTS

| | | |
|---|---|---|
| 4,572,909 | 2/1986 | Campbell et al. . |
| 4,879,303 | 11/1989 | Davison et al. . |
| 5,098,910 | 3/1992 | Becker et al. . |
| 5,155,120 | 10/1992 | Lazar et al. . |
| 5,500,434 | 3/1996 | Becker et al. . |
| 5,948,799 | 9/1999 | Cropp ................................. 514/356 |

FOREIGN PATENT DOCUMENTS

| | | |
|---|---|---|
| 0265685 | 4/1988 | (EP) . |
| 9220342 | 11/1992 | (WO) . |

OTHER PUBLICATIONS

Ramo et al., Amlodipine, a long acting calcium antagonist drug . . . , Am. J. Cardiol., vol. 64/17, pp. 781–831 (1989).*

Pieper, John., Evolving role of calcium channel . . . , vol. 16/2, pp. 43s–49s, (1965).*

Cohn, J., ACE–inhibitors in nonischemic heart failure . . . , European Heart Journal, vol. 16, pp. 133–136, (1995).*

Eur. J. Clin. Pharmacol., 1994, 285–9, Sun, J.X. et al: "Pharmacokinetic interaction study between benazepril and amlodipine in healthy subjects".

J. Am. Coll. Cardiol., 1993, 22/4 Suppl. A (139A–144A), USA, Elkayam U. et al: "Calcium channel blockers in heart failure".

American College of Cardiology 40th Annual Scientific Session, Atlanta, Georgia, USA Mar. 3–7, 1991. J AM Coll Cardiol, 17 (2 Suppl. A). 1991. 274A, ZP000578571 Packer M et al: "Randomized Multicenter Double–blind Placebo–Controlled Evaluation of Amlodipine in Patients with Mild–to–Moderate heart Failure".

Drugs, 1994, 47/Suppl. 4 (47–58), Cohn J. N.: "Vasodilators in heart failure. Conclusions from V–HeFT II and rationale for Y–HeFT III".

Prakash C. Deedwania, Arch Intern Med, vol. 150, Sep. 1990, pp. 1798–1805.

* cited by examiner

Primary Examiner—William R. A. Jarvis
Assistant Examiner—Vickie Kim
(74) Attorney, Agent, or Firm—Peter C. Richardson; Gregg C. Benson; James T. Jones

(57) ABSTRACT

Methods of treating congestive heart failure in a mammal, especially a human, by co-administration of (1) amlodipine, a pharmaceutically acceptable salt of amlodipine; (2) an ACE inhibitor; and optionally (3) a diuretic and/or (4) digoxin.

11 Claims, No Drawings

US 6,245,787 B1

COMPOSITION CONTAINING AMLODIPINE OR A PHARMACEUTICALLY ACCEPTABLE SALT THEREOF, AND AN ACE INHIBITOR

This is a National Stage filing under 35 USC 371 based on PCT/IB96/00145 filed internationally on Feb. 26, 1996, which was filed as a continuation of U.S. application Ser. No. 08/405,108 filed on Mar. 16, 1995, now abandoned.

This invention relates to compositions comprising (1) amlodipine, a pharmaceutically acceptable amlodipine acid addition salt, or felodipine and (2) an angiotensin converting enzyme (ACE) inhibitor. The invention further relates to methods for reducing mortality and/or morbidity in patients with congestive heart failure, comprising co-administering a congestive heart failure treating amount of a combination comprising amlodipine, a pharmaceutically acceptable amlodipine salt, or felodipine and an ACE inhibitor.

BACKGROUND OF THE INVENTION

Congestive heart failure, regardless of its etiology, is characterized by a weakness of the myocardial tissue of the left and/or right ventricle of the heart to pump and circulate blood into systemic and/or pulmonary circulations. It is accompanied by circulatory and neurohumoral changes which result in failure to deliver sufficient blood and oxygen supply to peripheral tissues and vital organs. If left untreated, the health of a patient with congestive heart failure could progress to the point where the disease would be fatal.

Amlodipine, 3-ethyl-5-methyl-2-(2-aminoethoxymethyl) 4-(2-chlorophenyl)-1,4-dihydro-6-methylpyridine-3,5-dicarboxylate, and its pharmaceutically acceptable acid addition salts are calcium channel blockers known for their effectiveness in the treatment, inter alia, of congestive heart failure, see U.S. Pat. No. 5,155,120 to Lazar et al. Amlodipine is currently marketed as the besylate salt.

Felodipine, ±ethyl methyl-4-(2,3-dichlorophenyl)-1,4-dihydro-2,6-dimethyl-3,5-pyridine dicarboxylate, is also a calcium channel blocker. It is disclosed in U.S. Pat. No. 4,264,611 to Berntsson et al. and is currently marketed as the free base.

ACE inhibitors are well known in the art for their activity in inhibiting angiotensin converting enzyme, thereby blocking conversion of the decapeptide angiotensin I to angiotensin II. The principal pharmacological and clinical effects of ACE inhibitors arise from suppression of synthesis of angiotensin II. Angiotensin II is a potent pressor substance and, therefore, blood pressure lowering can result from inhibition of its biosynthesis, especially in animals and humans whose hypertension is angiotensin II related. ACE inhibitors are effective antihypertensive agents in a variety of animal models and are clinically useful for the treatment of hypertension in humans.

ACE inhibitors are also employed for the treatment of heart conditions such as angina. It is known that at least some ACE inhibitors can improve (i.e., decrease) morbidity and mortality in patient populations with heart conditions.

International application PCT/US92/03873, published as WO 92/20342, discloses pharmaceutical compositions containing a combination of an angiotensin II antagonist and a calcium channel blocker for use in the treatment of hypertension and congestive heart failure. The publication states that the particular compositions can further contain antihypertensives and/or diuretics and/or angiotensin converting enzyme inhibitors.

SUMMARY OF THE INVENTION

This invention provides compositions comprising
a compound selected from amlodipine, pharmaceutically acceptable salts of amlodipine, and felodipine; and
an ACE inhibitor.

The invention further provides methods for reducing morbidity and/or mortality in patients with congestive heart failure, comprising co-administering to a mammal, especially a human, in need of such treatment a congestive heart failure treating amount of a combination comprising:
a compound selected from amlodipine, pharmaceutically acceptable salts of amlodipine, and felodipine; and
an ACE inhibitor.

The phrase "with congestive heart failure" includes patients who are at risk of suffering from this condition relative to the general population, even though they may not have suffered from it yet, by virtue of exhibiting risk factors. For example, a patient with untreated hypertension may not have suffered from congestive heart failure, but is at risk because of his or her hypertensive condition.

Amlodipine besylate is preferred as the calcium channel blocker. "Co-administration" of a combination of amlodipine (or its salts, or felodipine) and an ACE inhibitor means that these components can be administered together as a composition or as part of the same, unitary dosage form. "Co-administration" also includes administering amlodipine and an ACE inhibitor separately but as part of the same therapeutic treatment program or regimen. The two components need not necessarily be administered at essentially the same time, although they can if so desired. Thus "co-administration" includes, for example, administering amlodipine plus an ACE inhibitor as separate dosages or dosage forms, but at the same time. "Co-administration" also includes separate administration at different times and in any order. For example, a patient may take one component of the treatment in the morning and the other component at night.

The method referred to above for reducing morbidity and/or mortality generally refers to benefits and/or survival in the long term. Clinical benefits may be observable within a few weeks, for example 2–3 weeks. It is preferred, however that co-administration be effected long term; that is for longer than 16 weeks, and prefereably longer than 6 months. It is noted that a variety of short term (less than 16 weeks) exercise and hemodynamic trials have demonstrated that the addition of amlodipine to ACE inhibitors for the treatment of heart failure is safe. Recent studies in heart failure with a variety of pharmacologic compounds have demonstrated that short-term gain may not be predictive of long-term benefit, however.

Other components may also be optionally included as part of the compositions or methods of this invention. When included, such optional components will generally include digoxin and/or a diuretic. As known in the art, digoxin is a glycoside obtained from the leaves of digitalis. Other forms of digitalis exist, although digoxin is the form employed completely, or nearly so, throughout the medical profession.

The invention is surprising because, as demonstrated by the clinical studies disclosed below, the combination of amlodipine and an ACE inhibitor decreases the morbidity and/or mortality of a patient population with congestive heart failure over and above that which can be attributed to an ACE inhibitor alone. This result is surprising because, although ACE inhibitors are known to be capable of improving morbidity and/or mortality in patients with congestive heart failure, calcium channel blockers are not known to produce such a desirable effect.

DETAILED DESCRIPTION

ACE inhibitors useful in the invention can be widely selected from among those known to the art. Such useful compounds include inhibitors such as benazepril, captopril, enalapril, enalaprilat, fosinopril sodium, lisinopril, pentopril, perindopril, quinapril hydrochloride, quinaprilat, ramipril, ramiprilat, trandolapril, zofenopril calcium, and the like.

A diuretic may optionally be included as part of the therapeutic regimen and may similarly be widely selected from among those conventionally known in the art. Useful diuretics include methyclothiazide, hydrochlorothiazide, torsemide, metolazone, furosemide, chlorthalidone, N-(5-sulfamoyl-1,3,4-thiadiazol-2-yl)acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

The active ingredients (amlodipine, a salt thereof, or felodipine plus an ACE inhibitor) can be co-administered as a single composition and as part of the same dosage form. They can also be co-administered separately at the same or different times. They can be administered orally, together or separately, in solid dosage forms such as capsules, tablets, and powders, or in liquid dosage forms such as elixirs, syrups, and suspensions. They can also be administered parenterally, together or separately, in sterile liquid dosage forms.

Gelatin capsules can also be made conventionally to contain the active ingredients and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration can contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents, also are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Although the generic name of amlodipine represents the free base, amlodipine can also be used in the form of a pharmaceutically acceptable acid addition salt, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methanesulfonate, ethanesulfonate, benzenesulfonate, or p-toluenesulfonate. Preferred is the besylate salt as disclosed in U.S. Pat. No. 4,879,303.

The various active components comprising (1) amlodipine, pharmaceutically acceptable amlodipine salt or felodipine, (2) ACE inhibitor, and optionally (3) digoxin and/or a diuretic will each be co-administered in amounts effective to treat congestive heart failure, said amounts being sufficient to decrease morbidity and mortality in a population of patients at risk of suffering from congestive heart failure. The amount of amlodipine administered will generally be 1–20 mg daily, preferably 5–10 mg daily when administered orally. The dose can be divided if desired, although no particular therapeutic advantage is seen in doing so.

If felodipine is used instead of amlodipine, it will generally be administered orally in an amount of 2.5–20 mg once daily, preferably 2.5–10 mg once daily.

The ACE inhibitor will be administered in an amount which varies according to the particular compound employed, but which will generally be within the amount generally known for the inhibitor when administered alone. Table 1 below gives typical and preferred oral dosage ranges for a number of well known ACE inhibitors.

TABLE 1

ACE INHIBITORS

| NAME | TYPICAL RANGE (mg/day) | PREFERRED RANGE (mg/day) |
|---|---|---|
| CAPTOPRIL | 1 mg–150 mg | 3.125 mg–40 mg |
| ENALAPRIL | 0.75 mg–60 mg | 1.25 mg–40 mg |
| ENALAPRILAT | 0.3 mg–40 mg | 0.3 mg–20 mg |
| FOSINOPRIL | 2.5 mg–160 mg | 5 mg–80 mg |
| LISINOPRIL | 2.5 mg–80 mg | 2.5 mg–40 mg |
| QUINAPRIL | 2.5 mg–120 mg | 5 mg–80 mg |
| BENAZEPRIL | 2.5 mg–160 mg | 2.5 mg–80 mg |
| RAMIPRIL | 0.625 mg–80 mg | 1.25 mg–40 mg |
| TRANSOLAPRIL | 0.125 mg–10 mg | 0.25 mg–6 mg |

The same holds true for the particular diuretic which may optionally also be employed. Table 2 below gives typical and preferred oral dosage ranges for use in the invention for a number of well known diuretics.

TABLE 2

DIURETIC DOSAGES

| DIURETIC | TYPICAL RANGE (mg/day) | PREFERRED RANGE (mg/day) |
|---|---|---|
| BENDROFLUMETHIAZIDE | 1.25 mg–40 mg | 2.5 mg–20 mg |
| BENZTHIAZIDE | 3.125 mg–200 mg | 6.25 mg–100 mg |
| CHLOROTHIAZIDE | 62.5 mg–2000 mg | 125 mg–1000 mg |
| HYDROCHOROTHIAZIDE | 6.25 mg–200 mg | 6.25 mg–100 mg |
| HYDROFLUMETHIAZIDE | 6.25 mg–200 mg | 12.5 mg–100 mg |
| POLYTHIAZIDE | 0.25 mg–16 mg | 1 mg–4 mg |
| TRICHLOROMETHIAZIDE | 0.25 mg–16 mg | 1 mg–4 mg |
| CHLORTHALIDONE | 6.25 mg–200 mg | 12.5 mg–100 mg |
| INDAPAMIDE | 1.25 mg–20 mg | 2.5 mg–5 mg |
| METOLAZONE | 0.25 mg–30 mg | 0.5 mg–15 mg |
| QUINETHAZONE | 25 mg–200 mg | 50 mg–100 mg |
| BUMETANIDE | 0.25 mg–40 mg | 0.5 mg–20 mg |
| ETHACRYNIC ACID | 12.5 mg–400 mg | 25 mg–200 mg |
| FUROSEMIDE | 5 mg–2000 mg | 10 mg–200 mg |
| TOREMIDE | 2.5 mg–500 mg | 5 mg–300 mg |
| AMILORIDE | 2.5 mg–30 mg | 5 mg–10 mg |
| SPIRONOLACTONE | 12.5 mg–400 mg | 25 mg–200 mg |
| TRIAMTERENE | 12.5 mg–400 mg | 25 mg–200 mg |

The dosages for the various active ingredients will generally be somewhat lower than previously disclosed if administration is parenteral, for example intravenous enalaprilat.

Digoxin, if optionally employed, will be administered in an amount of 0.1 mg daily to 5 mg per week, usually once daily in an amount not exceeding 1 mg.

Of course, the attending physician can generally tailor the dose of each active ingredient in a given case.

The effectiveness of combination therapy comprising amlodipine or felodipine plus an ACE inhibitor in decreasing morbidity and/or mortality was shown by the following clinical study which illustrates the use of amlodipine, employed as the besylate salt in the study. The study was a randomized, double-blind, parallel group, placebo controlled multicenter study investigating the effects of amlodipine therapy on mortality and cardiac events in patients with severe heart failure. Patients entering the trial received background therapy consisting of an ACE inhibitor, digoxin, and diuretic. Investigators were allowed to use a diuretic and ACE inhibitor according to their own choice since the study was intended to represent the usual and customary care of patients. The timing and frequency of administration of the ACE inhibitor and diuretic were not prespecified and were in keeping with the pharmacodynamic properties of the individual active agents. Amlodipine besylate was administered once daily each morning.

Stratification of patients by heart failure etiology was prespecified. Based on medical history patients were randomized into either of two strata, an ischemic stratum or a non-ischemic stratum. Following a screening visit, consenting and qualifying patients were randomly allocated to receive amlodipine or placebo orally in a double-blind fashion for a minimum of six months.

The purpose of the study was to evaluate the effect of amlodipine compared with placebo on combined mortality (cardiac and noncardiac deaths) and life-threatening cardiac events in patients with severe heart failure.

Patients with chronic heart failure were enrolled at 105 centers. Patients were eligible if they had heart failure for at least 2 months. All patients were symptomatic (i.e., experiencing fatigue, palpitations or dyspnea) at rest, or upon minimal exertion (i.e., walking across a room or down a hallway) despite adequate treatment with ACE inhibitors, digoxin, and diuretics for at least 2 months. Heart failure was predominantly systolic with left ventricular ejection fraction lower than 30%. Patients were excluded if they demonstrated NYHA symptoms within two months of screening, or had a primary valvular or pericardial disorder or obstructive or hypertrophic cardiomyopathy. Patients were also excluded if they had unstable angina or a recent myocardial infarction or cardiac procedure; if they had a history of sustained ventricular arrhythmias or sudden death; or if they were receiving calcium channel antagonists, beta-adrenergic blockers, oral levodopa, cardiodepressant antiarrhythmic drugs (and/or including propafenone, moricizine, sotalol), direct acting vasodilator drugs (although short- and long-acting nitrates were permitted). Patients were also excluded if they had any of the following: systolic blood pressure less than 84 mmHg or greater than 160 mmHg, or diastolic blood pressure greater than 90 mmHg; clinical evidence of digoxin toxicity; second or third degree AV-block not treated with a functional pacemaker; severe primary lung disease or respiratory failure; or any clinically important laboratory abnormality.

Following a baseline evaluation qualifying patients were randomized to double-blind therapy with amlodipine or matching placebo. Randomization was stratified based on whether the patient had coronary artery disease as the cause of heart failure. Study medication was dispensed in identically matching amlodipine and placebo tablets with individually coded bottles prepared for each patient. The patients received amlodipine or placebo in a single tablet daily for 2 weeks, after which the dose was increased to two tablets daily, unless the lower dose was not tolerated. For amlodipine this corresponded to 5 mg and then 10 mg daily. Patients were followed every one to 3 months until the completion of the study. Background therapy (ACE-inhibitor, digoxin, and diuretic) was adjusted as clinically indicated. Open-label therapy with amlodipine was not permitted throughout the course of the trial.

The study was endpoint-driven. The primary endpoint was combined risk of cardiac morbidity and all-cause (cardiac and non-cardiac) mortality. A morbid event was considered an endpoint if there was evidence of deterioration of heart failure (acute pulmonary edema or severe hypoperfusion), acute myocardial infarction, or life-threatening ventricular arrhythmia requiring therapy. Separate secondary analyses were performed for all-cause mortality and cardiovascular mortality. All endpoints were adjudicated and deemed final by an independent classification committee blinded to treatment assignment. An independent Data and Safety Monitoring Board (DSMB) was established to monitor the accumulating data for evidence of benefit or harm to patients enrolled in the trial that could have been attributed to one of the treatment arms.

The primary objective of the study, as specified in the original protocol, was to compare the effect of amlodipine with placebo on combined mortality (cardiac and non-cardiac death) and life-threatening cardiovascular events. Secondary analyses were performed for: 1) all-cause mortality; and 2) cardiovascular mortality. The sample-size for the trial was estimated to be 800, based on the assumption of a one-year combined event rate of 40%. The study was designed to have a power of 90 percent (two-tailed) to detect a difference of 25 percent in event rate between the two treatment groups. Since it was recognized that any estimate of event rate made before the study might be inaccurate, it was planned that the trial should continue until 190 patients receiving placebo had reached a primary endpoint, as deemed by the Data and Safety Monitoring Board. As per protocol, enrollment in the trial continued until a total of 190 events occurred in the placebo group, and then all patients were followed for an additional 6 months. Accrual was extended to 1100 in order to protect against unexpectedly low event rates or poor compliance. A total of 1153 patients were recruited for the study.

Interim statistical analyses were performed at pre-specified times by an independent statistical center in order to monitor patient safety and treatment efficacy. Each interim data safety report presented all aspects of the study from data collected for each patient. The independent Data and Safety Monitoring Board reviewed each interim safety report, with primary emphasis placed on the evaluation of the primary endpoint events, as well as overall mortality. To protect against increasing the rate of false positive errors due to interim analyses, the Lan-DeMets procedure (Biometrika, 70, 659–663, 1983) was applied, with an O'Brien-Fleming (Biometrics, 35, 549–556, 1979) type of boundary. Baseline characteristics for the two treatment groups were compared by the Wilcoxin statistic (for continuous variables) and the chi-square statistic for categorical. Survival curves were constructed by use of the Kaplan-Meier estimate and differences between the curves were tested for significance by the log-rank test. The survival analyses included all randomized patients. All deaths were reported according to the etiology of heart failure (ischemic, non-ischemic) and the intention to treat principle was applied. Differences between treatment groups in events after randomization were analyzed by the t-test or chi-square test, as appropriate.

Of the 1153 patients enrolled in the study, 571 patients were assigned to treatment with amlodipine and 582 to treatment with placebo. A total of 875 male (76%) and 278 female (24%) patients participated in the study. The two treatment groups were similar in all their pre-treatment characteristics, with no notable imbalance between treatment arms with the possible exception of history of antiarrhythmic use being more prevalent on the placebo arm (25%) as compared to the amlodipine arm (20%). Less than two thirds (738, 64%) of the patients accrued were of ischemic etiology. As anticipated, there were fewer NYHA IV patients (222, 19%) than NYHA III (930, 81%). One patient was randomized despite being diagnosed with NYHA II symptoms. Duration of heart failure (median) in the amlodipine group was 2.7 years and 2.8 years in the placebo group. The median left ventricular ejection fraction and cardiothoracic ratio were 21% and 0.6 respectively, in both treatment groups. The duration of follow-up ranged from 2 to 1008 days (mean 418.6 days) in the amlodipine group and 3 to 1038 days (mean 412.9 days) in the placebo group.

The results are summarized as follows.

Primary and Secondary Analyses: During the course of the study there were 468 primary endpoints, 222 events in amlodipine-treated patients, and 246 events in placebo (p=0.30). In the evaluation of all-cause mortality patients treated with amlodipine experienced fewer deaths than those treated with placebo (190 vs. 223, respectively; p=0.07). The data was tested for the presence of interaction effects between etiology (pre-specified stratification) and treatment. A significant interaction between treatment and etiology was detected for the combined primary endpoint (p=0.04) and for all-cause mortality (p=0.004). That is, the effects of treatment were different in the ischemic and nonischemic subgroups. In such a situation, it is appropriate to base inferences on separate analyses in each subgroup. Conversely, it is statistically questionable to pool the interacting subgroups into a common analysis. Accordingly, treatment effects were examined in the separate etiology strata following conventional statistical procedure. In the ischemic stratum there was no difference in the number of events in the amiodipine and placebo treatment arms for the primary endpoint (164 and 168, respectively; p=0.74). However, in the nonischemic stratum there were 58 primary endpoints reported in the amlodipine group compared to 78 events in the placebo group, with an overall 31% reduction in the risk of experiencing a primary endpoint (95% Cl for the hazard ratio 0.490 to 0.982) which was statistically significant (p=0.03). In examining thetreatment effect on all-cause mortality in ischemic patients there was no difference between treatment groups (p=0.87). However, a striking reduction was observed in all-cause mortality in nonischemic patients treated with amlodipine. There were 45 deaths in the amlodipine group and 74 deaths in the placebo group, with overall a 46% reduction in the risk of death (95% Cl for the hazard ratio 0.373 to 0.796), which was statistically significant (p=0.0009).

In this double-blind study, the clinical efficacy and safety of amlodipine was evaluated in 1153 patients with chronic heart failure. All patients received background therapy with digoxin, diuretics and an angiotensin converting enzyme inhibitor. Overall, amlodipine proved to be safe in patients with NYHA III and IV heart failure. There was no difference between amlodipine and placebo on the primary endpoint of combined morbid and fatal events. There was a positive trend (p=0.07) in favor of amlodipine in the secondary endpoint of all-cause mortality. Furthermore, there was a significant treatment-etiology interaction for both primary and secondary endpoints. In the ischemic etiology stratum amlodipine had no detrimental effects on primary and secondary endpoints. More importantly, however, amlodipine was found to have significant positive effects on both primary and secondary endpoints in patients with nonischemic etiology. Amlodipine resulted in a significant reduction in combined morbid and fatal events as compared to placebo. There was a larger and even more striking benefit from drug on the secondary endpoint of all-cause mortality. Amlodipine caused a significant and substantial reduction in all-cause mortality, as compared to placebo. The dramatic reduction in primary and secondary endpoints with amlodipine are even more striking when it is noted that these effects are in addition to any and all benefits derived from the combination of angiotensin converting enzyme inhibitors, digoxin, diuretic, or any component thereof.

What is claimed is:

1. A method for reducing morbidity and/or mortality in a mammal with nonischemic congestive heart failure, comprising co-administering to said mammal congestive heart failure treating amounts of:

a compound selected from amlodipine and pharmaceutically acceptable salts thereof; and an ACE inhibitor.

2. A method as defined in claim 1, wherein said mammal is a human.

3. A method as defined in claim 2, wherein said compound is the besylate salt of amlodipine.

4. A method as defined in claim 2, wherein said ACE inhibitor is selected from the group consisting of benazepril, captopril, enalapril, analaprilat, fosinopril sodium, lisinopril, pentopril, perindopril, quinapril hydrochloride, quinaprilat, ramipril, ramiprilat, trandolapril, and zofenopril calcium.

5. A method as defined in claim 2, further comprising co-administering a diuretic.

6. A method as defined in claim 5, wherein said diuretic is selected from the group consisting of methyclothiazide, hydrochlorothiazide, torsemide, metolazone, furosemide, chlorthsalldone, N-(5-sulfamoyl-1,3,4-thiadiazol-2-yl)acetamide, triamterene, chlorothiazide, indapamide, bumetanide, amiloride, spironolactone bendroflumothiazide, benzthiazide, cyclothiazide, quinethazone, hydroflumethiazide, polythiazide, trichlormathiazide , and ethacrynic acid.

7. A method as defined in claim 2, further comprising co-administering digoxin.

8. A method as defined in claim 2, wherein co-administration is effected for longer than 16 weeks.

9. A method as defined in claim 8, wherein co-administration is effected for longer than six months.

10. A method for reducing morbidity and/or mortality in a mammal with nonischemic congestive heart failure, comprising co-administering to said mammal congestive heart failure treating amounts of:

a compound selected from amlodipine and pharmaceutically acceptable salts thereof;

an ACE inhibitor;

a diuretic, and digoxin.

11. A method as defined in claim 10, wherein:

said compound is the besylate salt of amlodipine;

said ACE inhibitor is selected from the group consisting of benazepril, captopril, enalapril, enalaprilat, fosinopril sodium, lisinopril, pentopril, perindopril, quinapril hydrochloride, quinaprilat, ramipril, ramiprilat, trandolapril, and zoefenopril calcium; and said diurectic is selected from the group consisting of methyclothiazide, hydrochlorothiazide, torsemide, metolazone, furosemide, chlorthalidone, N-(5-sulamoyl-1,3,4-thiadlazol-2-yl)acetamide, triamterene, chlorothiazide, indapamide, bumetanide, amiloride, apironolactone, bendroflumethiazide, benzthiazide, cyclothiazide, quinethazone, hydroflumethiazide, polythiazide, trichlormethazide, and athacrylic acid.

* * * * *